US009980981B2

(12) United States Patent
Gomperts et al.

(10) Patent No.: US 9,980,981 B2
(45) Date of Patent: May 29, 2018

(54) SOLUTION OF CARBON MONOXIDE FOR THE TREATMENT OF DISEASE, INCLUDING SICKLE CELL DISEASE

(75) Inventors: Edward D. Gomperts, Glendale, CA (US); Henry J. Forman, Studio City, CA (US)

(73) Assignee: CHILDREN'S HOSPITAL LOS ANGELES, Los Angeles, CA (US)

( * ) Notice: Subject to any disclaimer, the term of this patent is extended or adjusted under 35 U.S.C. 154(b) by 0 days. days.

(21) Appl. No.: 13/979,510

(22) PCT Filed: Jan. 10, 2012

(86) PCT No.: PCT/US2012/020710
§ 371 (c)(1),
(2), (4) Date: Jul. 12, 2013

(87) PCT Pub. No.: WO2012/096912
PCT Pub. Date: Jul. 19, 2012

(65) Prior Publication Data
US 2013/0309279 A1    Nov. 21, 2013

Related U.S. Application Data

(60) Provisional application No. 61/432,843, filed on Jan. 14, 2011, provisional application No. 61/434,639, filed on Jan. 20, 2011.

(51) Int. Cl.
*A61K 33/00* (2006.01)
*B01F 3/08* (2006.01)
*A61K 9/00* (2006.01)
*A61K 47/42* (2017.01)
*A61K 47/44* (2017.01)
*A61K 47/46* (2006.01)
*A61K 9/107* (2006.01)

(52) U.S. Cl.
CPC ............ *A61K 33/00* (2013.01); *A61K 9/0087* (2013.01); *A61K 9/0095* (2013.01); *A61K 47/42* (2013.01); *A61K 47/44* (2013.01); *A61K 47/46* (2013.01); *B01F 3/0876* (2013.01); *A61K 9/107* (2013.01)

(58) Field of Classification Search
CPC .... A61K 33/00; A61K 2300/00; A61K 45/06; A61K 47/46; A61K 9/0087; B01F 3/0876
See application file for complete search history.

(56) References Cited

U.S. PATENT DOCUMENTS

| 5,086,620 A | 2/1992 | Spears |
| 5,261,875 A | 11/1993 | Spears |
| 5,407,426 A | 4/1995 | Spears |
| 5,569,180 A | 10/1996 | Spears |
| 5,834,519 A * | 11/1998 | Spears ..................... A61K 9/10 424/43 |
| 5,922,305 A | 7/1999 | Spears |
| 5,958,377 A | 9/1999 | Spears |
| 6,169,117 B1 | 1/2001 | Spears |
| 6,197,279 B1 | 3/2001 | Spears |
| 6,238,645 B1 | 5/2001 | Spears |
| 6,344,489 B1 * | 2/2002 | Spears ..................... A23L 2/54 261/107 |
| 6,461,590 B2 | 10/2002 | Spears |
| 7,678,390 B2 | 3/2010 | Choi et al. |
| 7,976,743 B2 * | 7/2011 | Huang .................. A61K 9/127 264/4.1 |
| 2003/0039638 A1 | 2/2003 | Bach et al. |
| 2003/0219496 A1 | 11/2003 | Otterbein et al. |
| 2003/0219497 A1 | 11/2003 | Otterbein et al. |
| 2004/0005367 A1 | 1/2004 | Otterbein et al. |
| 2004/0228930 A1 | 11/2004 | Billiar et al. |
| 2004/0258772 A1 | 12/2004 | Otterbein et al. |
| 2008/0124436 A1 | 5/2008 | Roth et al. |
| 2011/0301531 A1 * | 12/2011 | Spears .................. B01F 3/0446 604/24 |

FOREIGN PATENT DOCUMENTS

JP     2008179569 A      8/2008
WO   WO-2012096912 A1   7/2012

OTHER PUBLICATIONS

Ikeda et al. Liver graft exposure to carbon monoxide during cold storage protects sinusoidal endothelial cells and emeliorates reperfusion injury in rats. Liver Transpl. 15(11):1458-1468 (2009).
Kohmoto et al. Carbon monoxide protects rat lung transplants from ischemia-reperfusion injury via a mechanism involving p38 MAPK pathway. Am J Transplant 7(10):2279-2290 (2007).
Nakao et al. A Single Intraperitoneal Dose of Carbon Monoxide-Saturated Ringer's Lactate Solution Ameliorates Postoperative Ileus in Mice. JPET 319:1265-1275 (2006).
Nakao et al. Ex vivo application of carbon monoxide in University of Wisconsin solution to prevent intestinal cold ischemia/reperfusion injury. Am J Transplant. 6(10):2243-2255 (2006).
Nakao et al. Ex vivo carbon monoxide prevents cytochrome P450 degradation and ischemia/reperfusion injury of kidney grafts. Kidney International 74:989-991 (2008).
Schmidt. The solubility of carbon monoxide and hydrogen in water and sea-water at partial pressures of about 10-5 atmospheres. Tellus 31:68-74 (1979).

(Continued)

*Primary Examiner* — Kyle A Purdy
(74) *Attorney, Agent, or Firm* — Wilson, Sonsini, Goodrich & Rosati

(57) ABSTRACT

The invention provides compositions and methods for delivering carbon monoxide (CO) to subjects suffering from inflammatory, cardiovascular, Sickle Cell, and other disease. The compositions are liquids, including Newtonian and non-Newtonian liquids, such as pastes, gels, foams, emulsions, and other non-gaseous compositions, in which CO is dissolved at an amount that, when administered to a patient, provides a therapeutically or prophylactically effective amount of CO to the patient. The compositions can be provided in many forms, including in bottles or cans.

12 Claims, No Drawings

(56) References Cited

OTHER PUBLICATIONS

Snedden et al. A new method for the measurement of gas solubility. Journal of Applied Physiology, American Physiological society80(4):1371-1378 (1996).

Yallop et al., "The associations between air quality and the number of hospital admissions for acute pain and sickle-cell disease in an urban environment." *British Journal of Haematology*, Issue 136, p. 884, 2007.

International Search Report and Written Opinion, PCT/US2012/020710, dated May 1, 2012.

* cited by examiner

SOLUTION OF CARBON MONOXIDE FOR THE TREATMENT OF DISEASE, INCLUDING SICKLE CELL DISEASE

CROSS-REFERENCE TO RELATED APPLICATIONS

This application relies on, and claims the benefit of the filing date of, U.S. provisional patent application No. 61/432,843, filed 14 Jan. 2011, and U.S. provisional patent application No. 61/434,639, filed 20 Jan. 2011, the entire disclosures of both of which are hereby incorporated herein by reference.

BACKGROUND OF THE INVENTION

Field of the Invention

The present invention relates to the fields of therapeutics and medical compositions. More specifically, the invention relates to methods of treatment for genetic, inflammatory, and other diseases that can be treated with therapeutic levels of carbon monoxide, including sickle cell disease, and to formulations and delivery vehicles that are useful in performing the methods.

Description of Related Art

At the present time, methods and devices for treatment of Sickle Cell Crises (referred to herein as "SCC") and its prevention are not adequate to manage the disease. The U.S. Centers for Disease Control and Prevention has estimated that 70,000 to 100,000 patients suffer from Sickle Cell Disease (referred to herein as "SCD") in the U.S., and the life expectancy of these afflicted individuals is only about 40 years. When a patient is admitted to hospital, treatment is symptom-based, mainly by way of morphine-analogue analgesics, fluid replacement, transfusions, and other supportive measures. Currently, the only consistent and reliable method of treatment of SCC is through blood transfusion. However, this treatment method is expensive and inconvenient, and can be dangerous. The use of hydroxyurea to prevent crises has been found to have marginal efficacy and to have side effects, and the response per patient is highly variable. It is also possible to cure SCD through bone marrow transplant, but this procedure is rarely used due to its inherent danger, its high cost, and the co-morbidities of the necessary treatment.

It is known that carbon monoxide (CO) is a poison at high concentrations, interfering with the ability of red blood cells to carry oxygen. It has been reported that hemoglobin (referred herein as "Hb") saturations of over 67% likely result in CO-induced death unless treatment is provided. Furthermore, Hb saturations of over 30% are reported to result in loss of consciousness, among other serious morbidities, and can result in death if maintained long-term. In addition, Hb saturations between 16% and 20% are reported to result in headache and visual evoked response abnormalities (Stewart RD. The effect of carbon monoxide on humans. Annu Rev Pharmacol 15: 409-423, 1975). As such, extreme caution must be used in situations where CO is present.

However, it is possible that CO can have positive effects in SCD and in other diseases and disorders. For example, it has been reported that CO extends the red cell life span in SCD patients. (Beutler, E., 1975, "The effect of carbon monoxide on red cell life span in sickle cell disease." Blood 46(2): 253-9.) It has also long been hypothesized that CO might play a role in preventing sickle cell formation by preventing the polymerization of hemoglobin (Sirs, J. A., 1963, "The use of carbon monoxide to prevent sickle cell formation", Lancet 1, 7288: 971-2). Further, it has been reported that CO might have a preventative effect on the occurrence of clinical symptoms of SCD. (Yallop, D., E. R. Duncan, et al., 2007, "The associations between air quality and the number of hospital admissions for acute pain and sickle-cell disease in an urban environment." Br J Haematol 136(6): 844-8.) The Yallop study documents that there is a decrease in hospital admissions of patients with SCC on days with higher CO content in the breathed air.

Recent research has also found that CO can have more widespread health benefits in multiple diseases and organ systems, including in cardiovascular, kidney, liver, lung, and intestine (Inge Bauer and Benedikt H J Pannen, "Bench-to-bedside review: Carbon monoxide—from mitochondrial poisoning to therapeutic use", Critical Care 2009, 13:220). Other research points to positive effects in inflammatory and cardiovascular disease (Foresti R, Bani-Hani M G, Motterlini R., "Use of carbon monoxide as a therapeutic agent: promises and challenges", Intensive Care Med. 2008 Apr; 34(4):649-58. Epub 2008 Feb. 20).

In view of the proposed beneficial effects of CO on certain diseases and disorders, a number of efforts using different delivery mechanisms have been made to employ CO as a treatment for disease. These include: delivery of CO gas via pulmonary delivery (Motterlini, R., Otterbein L., "The therapeutic potential of carbon monoxide", Nat Rev Drug Discov. 2010 Sep;9(9):728-43); the delivery of CO bound to a non-ferrous metal in a small molecule via intravenous infusion, intra-peritoneal injection, or oral ingestion (Motterlini, R., Otterbein L., "The therapeutic potential of carbon monoxide", Nat Rev Drug Discov. 2010 Sep;9(9):728-43); and the delivery of CO bound to a chemically modified human or bovine hemoglobin tetramer via intravenous infusion (Vandegriff, K. D., M. A. Young, et al. (2008). "CO-MP4, a polyethylene glycol-conjugated haemoglobin derivative and carbon monoxide carrier that reduces myocardial infarct size in rats." Br J Pharmacol 154(8): 1649-61; United States patent application publication number 20100311657 Abuchowski, Abraham et al. "HEMOGLOBIN COMPOSITIONS" December 9, 2010; and United States patent application publication number 20090082257 Winslow, Robert M. "MalPEG-Hb conjugate-containing compositions for delivering carbon monoxide (CO) to cells" Mar. 26, 2009). However, these efforts face a number of significant problems and shortcomings.

With regard to delivery of CO gas via inhalation, a number of problems exist that have precluded its clinical use. One of the primary reasons for the lack of clinical use relates to the importance of dosage in CO administration. The efficacious dose of CO is relatively close to its toxic dose. This makes pulmonary delivery difficult given differences in lung function in various diseases, including in SCD. A second complication is that CO is excreted through the lungs. As such, pulmonary delivery of CO requires uptake and excretion through the same organ, significantly complicating pharmacokinetics and determinations of safety. Another challenge with pulmonary delivery is that pulmonary delivery is inconvenient for patients given the discomfort of utilizing a breathing apparatus and the restriction on patient mobility given the need to be close to the breathing apparatus during dosage periods. This is a potentially significant matter, as inconvenience for patients is highly correlated to a lack of patient compliance. Moreover, the inherent toxicity of CO and its odorless, colorless properties make pulmonary delivery use challenging. Storing the amount of CO that would be needed to treat a patient long-term could, in the case of the home, put the patient and other family members in danger, and, in the case of the hospital, would require novel and costly safety precautions such as monitoring and venting before use, and even with such safeguards could put hospital staff in danger.

The utilization of small molecule transition metal-based carriers of CO (referred to herein as Carbon Monoxide Releasing Molecules or "CORMs") also presents significant challenges for clinical deliver of CO. In linking carbon monoxide to a transition metal, the toxicity of the transition metal is added to the inherent toxicity CO. This transition metal toxicity can limit the acceptable dose and, for certain metals, prevents use in humans completely. Ruthenium and Molybdenum are two of the more widely used transition metals in forming CORMs, and these metals have been categorized as metals of significant safety concern by the European Medicines Agency (EMEA COMMITTEE FOR MEDICINAL PRODUCTS FOR HUMAN USE (CHMP), "GUIDELINE ON THE SPECIFICATION LIMITS FOR RESIDUES OF METAL CATALYSTS OR METAL REAGENTS", London, 21 Feb. 2008, Doc. Ref. EMEA/CHMP/SWP/4446/2000). This high potential toxicity of CORMs due to the transition metal carriers prevents the use of CORMs in certain indications due to potentially toxicity-limited dosage and also through a more difficult risk:benefit ratio due to the added risk of the transition metal. Particularly unstable patients, including SCD patients, can be particularly at risk. In addition, the toxicity of transition metal carriers presents a significant barrier to recurrent use of CORMs in chronic indications. As SCD is an inherited lifelong condition, long term use of CORMs as a therapy for prevention of SCC is unlikely to be safe as the transition metal carriers will accumulate over time, aggravating the potential toxicity. In summary, the use of transition metal compounds as CO carriers has serious drawbacks as compared to less toxic approaches.

The use of chemically modified hemoglobin tetramers as carriers of CO (cell free CO-Hb) also presents toxicity-related issues. It has been demonstrated that certain significant safety events are associated with the clinical use of hemoglobin tetramer-based oxygen carriers, including myocardial infarction and death, among others (Natanson C, et. al. "Cell-free hemoglobin-based blood substitutes and risk of myocardial infarction and death: a meta-analysis", JAMA. 2008 May 21;299(19):2304-12). The potential toxicity of cell free CO-Hb due to the use of cell free hemoglobin as a CO carrier prevents the use of CO-Hb in certain indications due to potentially toxicity-limited dosage and also through a more difficult risk:benefit ratio due to the added risk of the hemoglobin tetramer. Particularly unstable patients, including SCD patients, can be particularly at risk. In addition, the toxicity of cell free Hb in addition to the potential problematic iron load presents a significant barrier to recurrent use of CO-Hb in chronic indications, including for use in prevention of SCC.

In addition, it has long been known that CO, as most gases, is soluble at low levels at ambient pressure in aqueous solutions. Solutions have previously been prepared in academic laboratories to demonstrate this fact. In addition, aqueous solutions have previously been prepared at ambient pressure and between 4° C. and 21° C., and used ex vivo in non-human studies in order to determine whether delivery of CO by such solutions could improve outcomes in the transplantation of gut, liver, and lung tissues (Nakao A et. al. "Ex vivo application of carbon monoxide in University of Wisconsin solution to prevent intestinal cold ischemia/reperfusion injury", Am J Transplant. 2006; 6(10):2243-2255; Ikeda, A et. al. "Liver graft exposure to carbon monoxide during cold storage protects sinusoidal endothelial cells and emeliorates reperfusion injury in rats", Liver Transpl. 2009 November ; 15(11): 1458-1468; Nakao A et. al. "Ex vivo carbon monoxide prevents cytochrome P450 degradation and ischemia/reperfusion injury of kidney grafts", Kidney International. 2008; 74:989-991). One study also looked at using such a solution prepared at room temperature and pressure and injected intraperitonealy (referred to herein as "IP") to investigate whether such a solution could ameliorate postoperative ileus in mice (Atsunori N, et. al., "A Single Intraperitoneal Dose of Carbon Monoxide-Saturated Ringer's Lactate Solution Ameliorates Postoperative Ileus in Mice", JPET 319:1265-1275, 2006). However, the use of this solution was severely limited. First, in preparing the solution at room temperature and pressure, the amount of dissolved CO was very low. This preparation methodology was necessary in this case because injecting a cold solution could be harmful if directly injected into the peritoneum and, moreover, as the liquid warmed, the CO would bubble out of the solution into the peritoneum which likely would cause potentially severe complications. In addition, while IP delivery is used in non-human research, it is rarely used in treating human disease for both safety and convenience reasons. First, the potential for infection in IP injection is significant, which creates an additional risk to this delivery route. In addition, the inconvenience for patients due to IP delivery can correspond to a lack of patient or physician compliance. Also, in order to allow home IP infusion, a permanent access into the peritoneal space would have to be placed in the patient, similar to that used in IP dialysis. This would add significant inconvenience and also potential morbidities, such as risk of infection, as compared to a non-IP delivery route. Moreover, the IP delivery route relies upon provision of a small amount of CO locally, using direct delivery to the gastrointestinal tract, which is inherently limiting with regard to the treatment of disease.

In summary, to date, there has been no widely suitable, convenient, and safe method for delivery of CO in amounts that would be therapeutic to treat diseases and disorders while avoiding toxicity and providing the necessary level of convenience to those in need.

SUMMARY OF THE INVENTION

The present invention provides a new way to treat disease, including cardiovascular, inflammatory, Sickle Cell, and other diseases for which CO can be used therapeutically. The present invention provides a method whereby CO is dissolved or entrapped in a liquid and the liquid is administered to a patient through the gastrointestinal (GI) tract or intravenously (IV) in an amount that delivers a treatment-effective amount of CO to the patient. The method of the invention safely administers CO to the afflicted patient, and provides a solution to a long-felt need in the art for a safe treatment method and delivery vehicle for CO. As used herein, the term "liquid" is given its broadest reasonable meaning, and thus includes both Newtonian liquids and non-Newtonian liquids. It thus includes compositions in which the main component, by weight, is a liquid. The term thus includes pastes, gels, and emulsions. It likewise includes foams in which CO bubbles are entrapped. For ease of reference, within the present disclosure, reference is made to "liquids" in which CO is "dissolved". However, it is to be understood that such references are not limited to Newtonian liquids in which CO is in solution, but rather to all liquids, pastes, gels, emulsions, foams, etc. in which gaseous CO is dissolved, entrapped, etc. It is believed that this is the first report of in vivo delivery of a CO-containing liquid through the GI tract or IV for therapeutic or prophylactic purposes. The invention allows for delivery of set (i.e., predetermined) amounts of CO to a patient systemically to treat disease. The CO-containing liquid is, in exemplary embodiments, delivered orally or by injection or infusion.

In a first aspect, the invention provides a liquid composition containing CO dissolved in an amount sufficient for delivery of the CO to a patient (used herein interchangeably with "subject" and "person in need"), wherein delivery to the patient results in an effective treatment on a disease or disorder that is treatable with CO. Unlike CO-containing liquid compositions known in the art, the liquid composition according to the present invention has a CO concentration that is sufficiently high that an effective amount of CO can be delivered to the patient in a convenient volume of liquid. That is, CO-containing liquid compositions known in the art, such as those known for investigating the effect of CO on surgically altered tissues, have relatively low concentrations of CO, and are not suitable for in vivo delivery of CO to treat diseases and disorders. In contrast, the liquid composition of the present invention comprises a relatively high concentration of CO, and can be used for in vivo delivery of treatment-effective amounts of CO to patients. While not so limited, in general, the composition of the present invention comprises a water-based composition in which CO is dissolved. Preferably, the CO is in gaseous form in solution, and is not complexed with a metal or one or more Hb molecules or complexes. In exemplary embodiments, the liquid composition is a beverage, such as one provided in a sealable container.

In another aspect, the present invention provides a method for treating a patient suffering from, or at risk of developing, a disease or disorder that can be treated or prevented by administration of an effective amount of CO. In general, the method comprises administering to a patient a liquid composition containing CO dissolved in an amount sufficient for delivery of the CO to the patient, wherein administering the composition results in an effective treatment on a disease or disorder that is treatable with CO. Unlike prior attempts to administer CO via direct inhalation of gaseous CO into the lungs, the present invention uses a liquid composition that is administered via the GI tract or IV to deliver gaseous CO in vivo to the patient. In exemplary embodiments, the liquid composition is administered orally by way of drinking of the composition. The method of the invention can be practiced to treat a chronic disease or disorder, i.e., the step of administering can be repeated multiple times over a relatively long period of time (e.g., years) or over a relatively short period of time (e.g., a few days, a week, or the length of duration of an acute episode of a disease or disorder). The method can be practiced as a therapeutic method to treat an active disease or disorder. Alternatively, the method can be practiced to prevent development of a disease or disorder. The method further can be practiced to reduce the likelihood of developing a disease or disorder or to reduce the frequency and/or severity of clinical symptoms of a disease or disorder and/or its consequences on organ and body function.

In yet another aspect of the invention, methods of making a liquid composition containing CO dissolved in a treatment-effective amount are provided. In general, the method comprises dissolving CO in a liquid under conditions that allow for relatively high amounts of CO to dissolve into the liquid. Suitable conditions for aqueous compositions include relatively high pressure, relatively low temperature, or a combination of both. Suitable conditions for lipid/oil based compositions might not require relatively high pressure or relatively low temperature. In preferred embodiments, the method further comprises dispensing the liquid into a container, prior to, during, or after dissolving of the CO into the liquid. Preferably, the container is sealed upon dissolving of the CO into the liquid. Preferably, the head space of the container comprises CO. In exemplary embodiments, the liquid composition is a beverage, such as one provided in a sealable container. In exemplary embodiments, the liquid composition comprises a water-based composition in which the CO is dissolved. In other exemplary embodiments, the liquid composition comprises an oil- or fat-based foam in which CO bubbles are entrapped. Preferably, the method provides a liquid composition in which CO is in gaseous form in solution or entrapped in bubbles in a foam, and is not complexed with a metal or one or more Hb molecules or complexes.

An additional general aspect of the invention relates to a method of determining the appropriate dosing of the liquid composition is provided. The method generally comprises using one or more of the following to determine an appropriate dosing regimen: lung function, patient hemoglobin and red blood cell measurements, patient blood volume and the concentration of CO in the liquid. Techniques for performing such assays are known in the art and can be practiced without undue or excessive experimentation. The method can be practiced on a regular basis to monitor and, if necessary, adjust the dosing regimen. In embodiments, the method is a method of determining appropriate dosing of the liquid, where the method comprises titrating upwards the dosage of the liquid to determine optimal treatment. The method can include the measurement of one or more of the following: CO exhalation, lung function, CO-hemoglobin, and pharmacokinetics.

DETAILED DESCRIPTION OF EXEMPLARY EMBODIMENTS

Reference will now be made in detail to various exemplary embodiments of the invention. It is to be understood that the following discussion of exemplary embodiments is not intended as a limitation on the invention, as broadly disclosed herein. Rather, the following discussion is provided to give the reader a more detailed understanding of certain aspects and features of the invention.

Before embodiments of the present invention are described in detail, it is to be understood that the terminology used herein is for the purpose of describing particular embodiments only, and is not intended to be limiting. Further, where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which the term belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a protein" includes a plurality of such proteins (including multiple copies of the same protein and multiple different proteins) and reference to "the patient" includes reference to one or more patients, and so forth. Furthermore, the use of terms that can be described using equivalent terms include the use of those equivalent terms. Thus, for example, the use of the term "subject" is to be understood to include the terms "animal", "human", and other terms used in the art to indicate one who is subject to a medical treatment. As another example, the use of the term "disease" is to be understood to include the term "disorder" (and vice versa) and all other terms used in the art to indicate an abnormal or aberrant medical condition.

The present invention provides a liquid composition containing CO dissolved in an amount sufficient for delivery of the CO to a patient, wherein delivery to the patient results in an effective treatment for a disease or disorder that is treatable with CO. Due, at least in part, to the method of making the composition (as disclosed herein), the liquid composition of the present invention has a gaseous CO concentration that cannot be achieved using techniques known in the art for creating gaseous CO-containing compositions. More specifically, the composition of the present invention has a dissolved CO concentration of at least 30 milligrams per liter (mg/l). The upper limit of dissolved CO is dictated only by physics and chemistry.

In exemplary embodiments relating to aqueous compositions, the concentration of dissolved CO will generally not exceed 400 mg/l. For example, an effective concentration for convenient dosing of CO to treat SCC and SCD is between about 100 mg/l and 400 mg/l, although concentrations between about 50 mg/l and about 100 mg/l are also suitable for patients amenable to intake of relatively large volumes of liquid during treatment periods. Likewise, concentrations on the lower end of these ranges can be suitable for SCC or SCD patients, who typically have relatively low Hb levels, and thus do not require as high a dose of CO as patients having more normal levels of Hb. Although the skilled artisan will immediately understand that all particular values within the range of about 30 mg/l and about 400 mg/l are specifically contemplated by this application, the following concentration values, and the various ranges defined by the collection of specific values, provide convenient reference points for the practitioner to develop compositions according to the present invention: 30 mg/l, 35 mg/l, 40 mg/l, 45 mg/l, 50 mg/l, 55 mg/l, 57 mg/l, 60 mg/l65 mg/l, 70 mg/l, 75 mg/l, 78 mg/l, 80 mg/l, 85 mg/l, 90 mg/l, 95 mg/l, 100 mg/l, 105 mg/l, 110 mg/l, 115 mg/l, 120 mg/l, 125 mg/l, 130 mg/l, 135 mg/l, 140 mg/l, 145 mg/l, 150 mg/l, 155 mg/l, 160 mg/l, 165 mg/l, 170 mg/l, 175 mg/l, 180 mg/l, 190 mg/l, 200 mg/l, 210 mg/l, 225 mg/l, 250 mg/l, 275 mg/l, 300 mg/l, 325 mg/l, 350 mg/l, and 375 mg/l. Aqueous compositions according to the present invention can comprise any specific concentration value between 30 mg/l and 400 mg/l, can comprise any specific concentration range between 30 mg/l and 400 mg/l, or can contain a concentration of dissolved CO of at least any of the concentration values between 30 mg/l and 400 mg/l.

In exemplary embodiments relating to lipid/oil/fat-based compositions, the concentration of dissolved CO will generally not exceed 4,400 mg/l. For example, an effective concentration for convenient dosing of CO to treat SCC and SCD is between about 500 mg/l and 4,400 mg/l, such as between about 500 mg/l and 4,000 mg/l, although concentrations between about 75 mg/l and about 500 mg/l are also suitable for patients amenable to intake of relatively large volumes of such liquids during treatment periods. Likewise, concentrations on the lower end of these ranges can be suitable for SCC or SCD patients, who typically have relatively low Hb levels, and thus do not require as high a dose of CO as patients having more normal levels of Hb. Although the skilled artisan will immediately understand that all particular values within the range of about 30 mg/l and about 4,400 mg/l are specifically contemplated by this application, the following concentration values, and the various ranges defined by the collection of specific values, provide convenient reference points for the practitioner to develop compositions according to the present invention: 75 mg/l, 100 mg/l, 125 mg/l, 150 mg/l, 175 mg/l, 200 mg/l, 225 mg/l, 250 mg/l, 275 mg/l, 300 mg/l, 325 mg/l, 350 mg/l, 375 mg/l, 400 mg/l, 425 mg/l, 450 mg/l, 475 mg/l, 500 mg/l, 525 mg/l, 550 mg/l, 575 mg/l, 600 mg/l, 625 mg/l, 650 mg/l, 675 mg/l, 700 mg/l, 725 mg/l, 750 mg/l, 775 mg/l, 800 mg/l, 825 mg/l, 850 mg/l, 875 mg/l, 900 mg/l, 925 mg/l, 950 mg/l, 975 mg/l, 1000 mg/l, 1025 mg/l, 1050 mg/l, 1075 mg/l, 1100 mg/l, 1125 mg/l, 1150 mg/l, 1175 mg/l, 1200 mg/l, 1225 mg/l, 1250 mg/l, 1275 mg/l, 1300 mg/l, 1325 mg/l, 1350 mg/l, 1375 mg/l, 1400 mg/l, 1425 mg/l, 1450 mg/l, 1475 mg/l, 1500 mg/l, 1525 mg/l, 1550 mg/l, 1575 mg/l, 1600 mg/l, 1625 mg/l, 1650 mg/l, 1675 mg/l, 1700 mg/l, 1725 mg/l, 1750 mg/l, 1775 mg/l, 1800 mg/l, 1825 mg/, 1850 mg/l, 1875 mg/l, 1900 mg/l, 1925 mg/l, 1950 mg/l, 1975 mg/l, 2000 mg/l, 2050 mg/l, 2100 mg/l, 2150 mg/l, 2200 mg/l, 2250 mg/l, 2300 mg/l, 2350 mg/l, 2400 mg/l, 2450 mg/l, 2500 mg/l, 2550 mg/l, 2600 mg/l, 2650 mg/l, 2700 mg/l, 2750 mg/l, 2800 mg/l, 2850 mg/l, 2900 mg/l, 2950 mg/l, 3000 mg/l, 3100 mg/l, 3200 mg/l, 3300 mg/l, 3400 mg/l, 3500 mg/l, 3600 mg/l, 3700 mg/l, 3800 mg/l, 3900 mg/l, 4000 mg/I, 4100 mg/l, 4200 mg/l, 4300 mg/l, and 4400 mg/l. Lipid/oil/fat compositions according to the present invention can comprise any specific concentration value between 30 mg/l and 4400 mg/l, can comprise any specific concentration range between 30 mg/l and 4400 mg/l, or can contain a concentration of dissolved CO of at least any of the concentration values between 30 mg/l and 4400 mg/l.

The liquid composition of the present invention is not particularly limited in its components, although exemplary embodiments disclosed herein have shown to be superior in the amount of CO that can be dissolved. While not so limited in all embodiments, in exemplary embodiments, the liquid composition of the invention is a water-based composition. It is to be understood that the term "water-based composition" includes all compositions comprising water as a solvent, including, but not limited to: compositions in which water is the sole solvent; water-oil mixtures (e.g., water-in-oil and oil-in-water emulsions); aqueous solutions, suspensions, colloids, and dispersions; water-alcohol mixtures; and combinations of these.

It has unexpectedly been found that aqueous compositions comprising one or more "complex" components provides superior CO-dissolving capacity. "Complex" components, as used herein, are substances that are polymeric in nature, biologic in nature, such as those derived from fatty acids, or otherwise comprise at least one bonding interaction site for CO. Interactions can be physical (e.g., hydrophobic, Van der Waals), or chemical (e.g., ionic or covalent). Examples of complex components include, but are not limited to: proteins, polypeptides, and peptides; polysaccharides; lipids, fats, and oils; and alcohols having two or more carbon atoms. In some embodiments, lipid, protein, or both are present in the compositions. In these embodiments, it is preferable that the combined amount of protein and lipid be greater than 5% (w/v), and even as high as 40% lipid and protein, or higher. In some formulations, the composition comprises greater than 5% lipid and greater than 5% protein.

The precise chemical structures of the complex components are not particularly limited. Rather, it is sufficient that the complex components function to assist in increasing the solubility of CO in the composition. However, to aid the practitioner in selecting appropriate complex components, the following is a non-limiting listing of types of complex components: proteins and fats/oils/lipids/triglycerides of animal derivation, such as those in milk; proteins and fats/oils/lipids/triglycerides of plant derivation; mono-, di-, and poly-saccharides; vitamins; natural and artificial sweeteners; and natural and artificial flavorings. Any and all of the various molecules that are encompassed within these groups are included as part of the present invention. Those of skill in the art will immediately recognize such molecules without the need for an exhaustive listing herein.

In embodiments, the liquid composition of the invention takes the form of a beverage for oral consumption. Non-limiting examples of beverages according to the invention are: bottled water, such as fruit- or berry-flavored waters; dietary/nutritional supplements, such as those formulated for infants and young children (e.g., baby formula, such as Similac® (Abbott, Abbott Park, Ill.) and Enfamil® (Mead Johnson & Company, Glenview, Ill.)) or adults (e.g., Ensure® (Abbott, Abbott Park, Ill.), and Peptamen® and Nutren® (Nestle, Vevey, Switzerland)); liquid dairy or dairy-based products, such as milk, cream, yoghurt, or a milkshake; liquid soy or soy-based products, such as soy milk or soy yoghurt; liquid rice or rice-based products, such as rice drinks; sports drinks or dietary supplements, such as whey protein based drinks and Gatorade® (Pepsico, Purchase, N.Y.); coffee-based drinks, such as those supplemented with dairy products; and sugar-containing or sugar-free sodas. As discussed in more detail below, certain liquid compositions of the invention are supersaturated with CO at room temperature and atmospheric pressure. As such, certain beverages can be effervescent as a result of release of a portion of the supersaturated CO. This effervescent property can enhance the patient's experience when ingesting the beverage, and can improve compliance with a dosing regimen.

In embodiments, the liquid composition of the invention takes the form of a foam- or gel-based food product. For example, in some embodiments, the liquid composition is provided in the form of a gel, such as a gelatin or pudding, such as those commercially available under the Jell-O® brand (KraftFoods, Inc., Glenview, Ill.). Yet again, in some embodiments, the liquid composition is provided in the form of a foam, such as those commercially available under the Coolwhip® brand (KraftFoods, Inc., Glenview, Ill.) and ReddiWip® brand (ConAgra Foods, Inc., Omaha, Nebr.).

A beverage or food product according to the invention can be provided in a container. In preferred embodiments, the container is a sealable container of the type widely used for providing commercial beverages and food products to the public. Non-limiting examples of sealable containers for holding the beverage and/or food product are: plastic bottles with twist on/off tops; aluminum cans with pop tops; glass bottles with twist on/off tops; and glass bottles with crimp-sealed aluminum tops or tops made of other pliable metals. For convenience in delivering an effective amount of CO to a subject in need, in preferred embodiments, the amount of beverage or food product in a single container is an adequate volume of beverage or food product to supply a single dose of CO (e.g., 5 ml, 10 ml, 30 ml, 50 ml, 75 ml, 100 ml, 150 ml, 177 ml, 180 ml, 237 ml, 300 ml, 355 ml, 500 ml, one liter). As such, it is recognized that the liquid compositions of the invention can be provided such that a daily dosage for treatment of a disease or disorder (e.g., a symptom thereof) is conveniently provided in volumes of about 3 liters or less, such as 2.5 liters, 2 liters, 1.8 liters, 1.5 liters, 1 liter, 330 ml, 300 ml, 180 ml, 30 ml, or less. However, it is to be understood that, in situations where the beverage or food product is supplied in a re-sealable container (e.g., a bottle with a twist on/off cap), the amount of beverage or food product in the container can represent more than one dose of CO.

The invention thus provides products for practicing the method of the invention (discussed in detail below). The products can be products typically associated with medical procedures, such as solutions and containers containing solutions (e.g., IV bags). Alternatively, the products can be in the form of more easily administered products, such as canned or bottled solutions or foods. The technology is simple to apply, unlikely to be associated with significant side effects, and acceptable to the affected population, thus resulting in reliable utilization of the treatment method.

In summary, in various exemplary embodiments, the present invention provides a liquid composition comprising dissolved gaseous carbon monoxide (CO) in an amount of from 30 mg/l to 4400 mg/l in the liquid composition. In embodiments, the composition comprises dissolved gaseous CO in an amount of from 50 mg/l to 400 mg/l, from 75 mg/l to 750 mg/l, and from 550 mg/l to 4400 mg/l. In general, the dissolved CO is present in an amount sufficient to prevent or treat at least one clinical symptom of a disease or disorder affected by CO. Various diseases and disorders treatable with the composition are discussed below. In embodiments, in addition to dissolved gaseous CO, the composition further comprises at least one of: protein, lipid, fat, triglyceride, complex carbohydrate, sugar, sugar substitute, fruit juice, carbohydrate, cellulose, fiber, citric acid, artificial flavoring, natural flavoring, gum, pectin, ascorbic acid, preservative, saponin, oil, oil emulsion, pH buffer, and a salt. For the liquid portion of the composition, in exemplary embodiments, water, ethanol, or both are used. In embodiments, the liquid composition is one in which the amount of dissolved CO is greater than occurs under ambient temperature and pressure and at a pH of 7.0 and/or at pH of 7.0, atmospheric pressure, and 21° C. For example, the dissolved CO can be two or more times the amount dissolved under ambient temperature and pressure and at a pH of 7.0 and/or at pH of 7.0, atmospheric pressure, and 21° C.

As mentioned above, the liquid composition can comprise dissolved gaseous CO, or gaseous CO entrapped in bubbles, in an amount of at least 0.03 grams of gas per kilogram of water or other liquid (i.e., at least 30 mg/l). In embodiments, the amount of dissolved or entrapped CO is greater than 0.04 grams of gas per kilogram of water or other liquid. In embodiments, the amount of dissolved CO is equal to or greater than the amount that occurs under two atmospheres of pressure at 10° C. and at a pH of 7.0. In certain embodiments, the liquid composition is one in which dissolved or entrapped CO can be administered orally, intravenously, or otherwise through the gastrointestinal tract, and that contains no potentially toxic constituents other than CO.

The liquid composition of the invention enables one to treat a patient suffering from a disease or disorder, which is amenable to treatment with CO. Thus, one aspect of the present invention is a method for treating a patient suffering from, or at risk of developing, a disease or disorder and/or suffering from consequences of the disease or disorder on organ function that can be treated or prevented by administration of an effective amount of CO. Thought of another way, the method can be considered a method of treating a disease or disorder that can be treated or prevented by administration of an effective amount of CO. Broadly speaking, the method comprises administering to a patient a liquid composition comprising a therapeutically-effective or a prophylactically-effective amount of dissolved gaseous CO, wherein administering the composition results in an effective treatment for a disease or disorder that is treatable with CO. Administering can be accomplished by any suitable technique known in the art. However, it has been determined that administering via the GI tract or via IV infusion or injection is superior to other routes of administration. Administering via the GI tract is preferably accomplished through oral ingestion (e.g., drinking). However, the invention contemplates administration via other points in the GI tract, such as by way of an enema or by way of direct delivery to the small or large intestine. The invention also contemplates delivery via inhalation of an aerosolized or nebulized liquid and delivery via IP, IM, organ catheter, and subcutaneous injection. However, for reasons discussed herein, these routes of administration are less preferred.

Many diseases and disorders that can be treated with CO are chronic in nature. As such, long-term treatment is often necessary. The present invention is particularly well suited for treatment of such chronic diseases and disorders because it allows for long-term delivery of pre-defined and precisely regulated amounts of gaseous CO to a patient. Unlike delivery of airborne CO to the lungs via inhalation, the present invention, by delivery of gaseous CO dissolved in a liquid to the GI tract or via IV infusion to the blood system, delivers CO through an organ other than the lungs. While adjustments in the dosing regimen will likely be needed over a long course of treatment, avoidance of the lungs as the site of administration avoids a complicating factor for precise and accurate dosing, which is a significant consideration in view of the small difference in concentration of CO between therapeutic levels and toxic levels. The same can be said for administration via IV infusion, although oral ingestion is much more convenient and cost-effective.

The present invention is also well suited for treatment of acute episodes of diseases and disorders that can be treated with CO. Delivery of a composition according to the invention to the GI tract or to the blood stream allows for rapid dosing of CO to a patient. Systemic therapeutic CO levels can be achieved rapidly, thus allowing for reduction in clinical symptoms of a disease or disorder. Among the benefits provided by the invention is the limiting of the extent of damaged tissue and thus the extent of pain associated with SCC. More specifically, by quickly raising the CO content of the blood, the damage caused during SCC can be limited to the site of the original pain, thus reducing spread of the damage and pain. Furthermore, because a patient experiencing SCC will have been diagnosed with SCD (except, potentially, for the first episode of SCC), the appropriate amount of CO to be delivered can easily be determined, thus allowing for accurate and precise delivery of an effective, but not toxic, amount of CO to the patient.

The method of treating according to the invention is a method that treats patients suffering from diseases and disorders that can be treated with CO. Because the effective bioactive agent is known, and its role in treating the disease or disorder is known, the method according to the invention can be practiced both therapeutically to treat a disease or disorder, and prophylactically to prevent or delay onset of the clinical symptoms of a disease or disorder. That is, because CO is the active agent that reduces and, ultimately, eliminates the clinical symptoms of a disease or disorder encompassed by the present invention, it also is the active agent that prevents or delays onset of a clinical symptom of a disease or disorder encompassed by the present invention. For example, in the case of SCD, prophylactic treatment with CO can reduce or eliminate formation of sickle-shaped red blood cells, thus preventing or delaying onset of SCC and mitigating the complications of SCC. Of course, those of skill in the art will understand that the term "prevent" does not imply absolute prevention of any development and progression of a disease or disorder, but instead indicates blocking, to at least some extent, of the natural development or progression of the disease or disorder.

The method of the invention comprises administering a CO-containing liquid composition to a patient in need thereof. Although the invention contemplates performing the administering step a single time, the step of administering can be repeated any number of times. Indeed, in preferred embodiments, the step of administering is repeated a sufficient number of times to achieve a carbonmonoxy-hemoglobin (herein referred to as "CO-Hb") concentration suitable for the disease or disorder being treated. For example, for treatment of SCD, an average CO-Hb concentration of between 3% and 15%, more preferably between 3% and 12%, most preferably between 3% and 9%, such as about 3% to 6%, is desirable. It is known that the half-life of the alpha-phase of CO in the human bloodstream is about 4-6 hours. Therefore, an average CO-Hb concentration in the bloodstream can be achieved, for example, through a dosing regimen of four or fewer doses per day, preferably equally spaced, such as four doses per day (i.e., every six hours), three doses per day (i.e., one dose every eight hours), two doses per day (i.e., every twelve hours), or one dose per day. Due to the relatively high CO concentration achievable in a liquid composition according to the present invention, relatively small volumes of liquid composition can be administered per dose or per day, such as: 2 liters per day, 1.5 liter per day, 1 liter per day, 0.7 liter per day, 0.5 liter per day, 0.25 liter per day, and 0.1 liter per day, and other amounts disclosed herein. Dosing of small volumes improves patient compliance and provides an overall superior outcome for the patient. As there is no known detrimental effect to long-term exposure to CO at these levels, the daily administration can be performed indefinitely. Those of skill in the art will recognize that this concept is equally applicable to other diseases and disorders treatable with CO, and that the average CO-Hb level suitable for treatment of those diseases and disorders might be different, but can easily be determined.

The present invention is based, at least in part, on the understanding that dosing with CO must be well controlled due to the fact that the toxic level of CO is close to the therapeutic level. More specifically, it is generally recognized that levels of CO in the bloodstream that result in up to about 15% CO-Hb show effectiveness at reducing SCC without significant deleterious side effects or toxicity. However, it is also generally recognized that, at CO-Hb levels between about 16% and 20%, some toxicity is seen, and that at CO-Hb levels over 20%, toxicity and side effects are routinely seen. The present invention takes into account the closeness of effective dose levels without substantial untoward side effects or toxicity and dose levels that result in toxicity and side effects. The present invention provides products and treatment methods that conveniently, precisely, and reproducibly achieve an effective dosing of CO to patients while avoiding toxic levels and/or side effects.

Among the diseases and disorders that are encompassed by this invention, mention can be made of: hematological diseases, inflammatory diseases, ischemic diseases, and cardiovascular diseases. For example, the technology can be useful in treatment of hematological diseases such SCD. Further, the technology can be useful in inflammatory diseases, such as inflammatory bowel disease, Crohn's disease, ulcerative colitis, multiple sclerosis, rheumatoid arthritis, coronary ischemia, systemic inflammation, and inflammation associated with transplantation. Yet again, the technology can be useful in treatment of ischemic disease, such as, coronary ischemia, neural ischemia, organ ischemia, and shock-induced ischemia. Likewise, the technology can be useful in treating cardiovascular diseases, such as: vascular disease, ischemia/reperfusion, and decrease in lung function. Other non-limiting diseases and disorders that are applicable to the present invention include gastrointestinal diseases, such as post-operative ileus and transplantation; sepsis; kidney disease; and liver disease, such as ischemia/reperfusion and burn injury.

Exemplary embodiments of the invention relate to diseases of the blood or hematological diseases. Among the hematological diseases that can be treated according to the present invention are those involving abnormal hemoglobin, such as SCD, Hemoglobin C Disease, Hemoglobin SC Disease, and Hemoglobin S beta-thalassemia.

With regard to SCD, the present invention provides a new way to treat the disease, including prevention and treatment of SCC using gaseous CO. In treatment of SCC, the CO is delivered to a subject in need (i.e., patient) in an amount that affects at least one clinical symptom of SCC. In preferred embodiments, the method of treatment reduces or eliminates at least one clinical symptom of SCC, but in an amount that does not induce unacceptable levels of toxicity or adverse side-effects. In prevention of SCC, the CO is delivered to a subject in need (i.e., patient) on a regular basis in an amount that affects the number of SCC experienced by the subject in need. In preferred embodiments, the method of prevention reduces the number or severity of SCC experienced by the subject in need. Administration for treatment of SCD and SCC can be through any route suitable for a liquid. In preferred embodiments, administration is through oral ingestion of the liquid or via injection or infusion into the bloodstream. Although CO is toxic in high concentrations, it is non-toxic at the relatively low concentrations useful according to the present invention. Furthermore, because CO binds to hemoglobin S ("Hb-S") at a much higher affinity than does oxygen, and because Hb must be in non-gas bound configuration to polymerize (which results in sickle cell development), relatively low doses of CO can be used to prevent and treat SCD and SCC. The method may also comprise administering CO to a subject on a regular basis in an amount that is sufficient to reduce the number of SCC experienced by the patient and/or reduce the resulting organ damage caused by sickling. Organs affected include, but are not limited to, lungs, brain, heart, kidneys, bone, spleen, liver, endocrine glands, and male sex organs. The impact of sickling over time extends the degree of organ damage. In embodiments, the method is repeated regularly to provide a chronic treatment regimen.

While there are a number of ways to administer the CO to treat SCD and SCC, the most convenient is by way of or administration of a CO-infused liquid. CO absorbed through the GI system or injected into the bloodstream rapidly attaches to Hb, thus providing an effective and rapid treatment.

Treatment of SCC according to the methods of the invention can have the following effects for acute use: it can shorten the crises and alleviate the severity of the crises. Treatment of SCC according to the methods of the invention can have the following effects for chronic use: it can decrease the frequency of crises, it can decrease the severity of the crises, it can decrease the extent, progression, and frequency of organ damage, and it can outright prevent crises.

Delivery of CO to a patient via administration of liquid is most conveniently achieved using generally available containers, such as a metal can or glass or plastic bottle. The liquid and type of container is not particularly limited, with the exception that the liquid must allow for adequate levels of CO to dissolve, while the container must be fabricated of material that is sufficiently impermeable to CO and sufficiently pressure resistant. Of course, the practitioner will need to adjust the composition of the liquid in some situations to optimize CO dissolving into the liquid and thus absorption into the body of the patient. For example, the salinity, pH, sugar content, amount of organic compounds (e.g., alcohol), protein content, lipid content, etc. can be varied to optimize the taste, consistency, etc. of the composition, and the amount of CO that dissolves into the liquid and also to optimize CO absorption once delivered to the patient. Also, the pressure, temperature, and components in the composition during CO dissolution can be varied to optimize the amount of CO that dissolves into the liquid. Likewise, non-aqueous solutions of various constituents can be used, as well as aqueous or non-aqueous compositions that include undissolved constituents.

Among the many containers that can be used, mention may be made of: glass bottles, plastic bottles; and aluminum cans, and containers fabricated from combinations of glass, plastic, and aluminum and other metals.

CO has a number of medical properties and has shown promise in treating a variety of diseases. The primary challenge in using CO as a therapeutic given its potential toxicity is to deliver a small but sufficient amount of CO to treat disease without causing harm. Until now, it has not proven possible to do this.

There are a number of significant limitations to using the delivery of CO dissolved in liquid and used through the GI tract or IV for therapeutic or prophylactic purposes. These limitations have been overcome in the present invention. The primary barrier to date has been delivering sufficient quantities of CO. The solubility of CO in aqueous solutions is low at room temperature and normal atmospheric pressure (ATM). Thus, using approaches previously proposed in the art, which rely on dissolving CO into an aqueous composition at room temperature and at atmospheric pressure, the volume of liquid necessary to deliver a therapeutic dose of CO is logistically prohibitive. However, using the present invention, therapeutically useful levels of CO can be achieved. Table 1 provides a summary of volumes necessary to achieve a therapeutic dose providing an average increase of 9% CO-Hb, which provides an average CO-Hb level in the blood of about 7% on average without rising above 15% at any given time. The values are presented for SCD patients. Table 2 provides a similar summary of volumes necessary to treat patients having normal levels of Hb and normal lung function.

TABLE 1

| Temperature, Pressure | CO Concentration Achievable in Aqueous Composition (mg/L water) | Volume of Liquid Needed to Achieve Increase of 9% of CO-Hb in SCD Patients | Necessary Daily Volume of Liquid to Achieve Average Increase of 9% CO-Hb |
|---|---|---|---|
| 21° C.; 1 ATM | 25 | 2.54 L per 12 hrs | 5.1 L |
| 2° C.; 1 ATM | 40 | 1.59 L per 12 hrs | 3.2 L |
| 2° C.; 2 ATM | 80 | 0.79 L per 12 hrs | 1.6 L |
| 2° C.; 3 ATM | 120 | 0.53 L per 12 hrs | 1.1 L |
| 2° C.; 5 ATM | 200 | 0.32 L per 12 hrs | 0.6 L |
| 2° C.; 10 ATM | 400 | 0.15 L per 12 hrs | 0.3 L |

TABLE 2

| Temperature, Pressure | CO Concentration Achievable in Aqueous Composition (mg/L water) | Volume of Liquid Needed to Achieve Increase of 9% of CO-Hb in "Normal" Patients | Necessary Daily Volume of Liquid to Achieve Average Increase of 9% CO-Hb |
|---|---|---|---|
| 21° C.; 1 ATM | 25 | 4.52 L per 8 hrs | 13.6 L |
| 2° C.; 1 ATM | 40 | 2.83 L per 8 hrs | 8.5 L |
| 2° C.; 2 ATM | 80 | 1.41 L per 8 hrs | 4.2 L |
| 2° C.; 3 ATM | 120 | 0.94 L per 8 hrs | 2.8 L |
| 2° C.; 5 ATM | 200 | 0.57 L per 8 hrs | 1.7 L |
| 2° C.; 10 ATM | 400 | 0.28 L per 8 hrs | 0.8 L |

Tables 1 and 2 demonstrate that under ambient pressure, even at low temperature, it is not possible to achieve a CO concentration in solution that enables a therapeutic dose of CO using a volume of aqueous solution that can reasonably be taken orally by a patient in a 24 hour period.

In order to achieve a higher CO concentration that allows a volume of aqueous solution that can reasonably be taken orally in a 24 hour period, in the present invention a number of improvements over prior attempts in the art have been made.

First, in the present invention, in particular as it relates to embodiments wherein aqueous compositions are involved, CO is dissolved in an aqueous liquid under higher than ambient pressure. The use of pressure to dissolve the CO increases the achievable concentration of CO in solution. Tables 1 and 2 demonstrate the significantly increased CO concentrations achievable under pressure and the corresponding substantial decrease in the necessary amount of aqueous solution needed to provide an effective dose of CO. One of skill in the art will immediately recognize that lowering of the temperature below 2° C. and increasing the pressure above 10 ATM can achieve an even greater concentration of CO dissolved in the aqueous solution, and that the values presented in Table 1 are for demonstration purposes only. Although raising the pressure above 10 ATM might not be commercially practicable, it is technologically feasible at this time.

Tables 1 and 2 demonstrate that under greater than ambient pressure and low temperature, it is possible to achieve a CO concentration in solution that enables a therapeutic dose of CO in a volume of aqueous solution that can reasonably be taken orally by a patient in a 24 hour period. The volumes needed to be administered per day are well within amounts taken daily by many people. Thus, compliance by patients should be vastly improved as compared to any attempts at treatment with CO-containing liquids known in the art.

Second, the use of a GI formulation (e.g., a formulation for oral administration) overcomes a challenge of using a CO-infused aqueous composition as a therapeutic. An aqueous oral or GI formulation allows the use of a solution with CO dissolved under higher than ambient pressure and low temperature, enabling a therapeutic dose of CO. When CO is dissolved into solution under greater than ambient pressure, and the solution is then moved into an ambient pressure environment upon delivery of the solution, the CO gas will bubble out of solution (similar to liquid solutions containing dissolved $CO_2$). Bubbles of gas pose a substantial danger to a patient in many delivery mechanisms, such as IP and intravenous delivery, amongst others. However, the bubbling of CO gas out of solution in the stomach or intestine does not pose a substantial safety risk. Thus, the use of a delivery route that allows the bubbling of CO out of solution enables the use of this invention in therapeutic indications that require a high CO concentration. Also, dissolving CO into solution under temperatures close to or below 0° C. increases the CO saturation of the solution, as compared to dissolving CO at room temperature. The administration of a very cold solution poses discomfort and danger to a patient in many delivery mechanisms, such as IP and intravenous delivery, amongst others. However, the use of a cold liquid in the stomach or intestine does not pose a substantial safety risk or substantial discomfort. Thus, the use of a delivery route that allows the administration of a cold solution enables the use of this invention in therapeutic indications that require a high CO concentration. Furthermore, while the present invention contemplates dissolving CO into a liquid at relatively low temperatures, the CO need not be delivered to a patient by way of a cold liquid. For example, a CO-containing liquid composition can be prepared in a sealable container. Once sealed, the container need not be maintained at a cold temperature for the CO to stay in solution. Although a greater amount of CO will escape from solution if the container is opened at higher temperatures than at lower temperatures, ingestion (or other delivery) of the liquid to the patient in a relatively short time period after opening of the container will minimize loss of CO from the liquid.

Third, the present invention recognizes that complex liquid compositions are superior to water or relatively simple aqueous compositions for therapeutic delivery of CO. Prior attempts at delivering CO to cells used CO dissolved in water or in aqueous solutions of water and salts. According to preferred embodiments of the present invention, the liquid composition for delivery of CO is an aqueous composition that contains one or more relatively complex molecules, such as proteins, lipids, oils, alcohols, and/or carbohydrates. It has been found that the presence of these complex molecules allows greater CO solubility as compared to compositions lacking them. As such, inclusion of these complex molecules overcomes a challenge of using CO as a therapeutic. Preferred embodiments of the invention thus include administration of complex aqueous compositions comprising therapeutic concentrations of CO mixed with one or more lipids, proteins, or other substances that aid in increasing the concentration of CO in the aqueous composition.

Fourth, another characteristic of the present invention that overcomes a challenge with using CO as a therapeutic is the use in patients with low Hb concentrations, including those patients with SCD. As mentioned above, the amount of liquid that can be administered to a patient is a limiting factor given the relatively low solubility of CO in liquids. However, because the amount of Hb is lower in certain patient populations, such as those with SCD, therapeutic dosage levels of CO are likewise lower in such patients. The high concentration of CO possible in liquids according to the present invention allows greater ease of use, improved patient compliance, and an overall improvement in therapeutic effect, as compared to other treatments proposed in the art.

As discussed above, the invention provides a method of treating a patient suffering from a disease or disorder, or at risk of developing a disease or disorder, that can be treated or prevented by administration of CO. The invention thus provides for the use of a liquid composition comprising a therapeutically effective amount of CO in the treatment of a disease or disorder, or for the prevention of a disease or disorder, that can be treated or prevented by administration of CO. The invention further provides for the use of a liquid composition comprising a therapeutically effective amount of CO in the preparation of a medicinal composition for the treatment or prevention of a disease or disorder that can be treated with CO.

In yet another general aspect of the invention, methods of making a liquid composition containing CO dissolved in a treatment-effective amount are provided. Previous attempts in the art to create a liquid composition containing dissolved gaseous CO involved dissolving CO in an aqueous liquid at ambient temperature and atmospheric pressure, resulting in a composition that is unsuitable for use as an in vivo therapeutic or prophylactic agent due to the low CO content in the liquid. The present invention, in contrast, achieves a therapeutically- and prophylactically-effective agent through the use of a preparation method that includes the use of high pressure, cold temperature, or a combination of the two. Preferably, the method also includes the use of a liquid composition that includes one or more complex components, which aid in increasing the concentration of CO dissolved in the composition.

The method of making a CO-containing liquid composition typically comprises subjecting a liquid composition to a high pressure while exposing the composition to gaseous CO for a sufficient amount of time to achieve an adequately high concentration of CO in the liquid composition to provide a therapeutically-effective and/or prophylactically-effective composition. However, it is to be noted that, in certain embodiments in which the compositions comprise lipids, fats, or oils, introduction of therapeutic levels of CO might not require the use of higher than atmospheric pressure. In preferred embodiments, the step of exposing comprises infusing CO into the liquid composition by bubbling through a cannula, aerator, or other equivalent device or method. In some embodiments, the liquid composition is subjected to mixing or stirring during the process of exposing to CO in order to facilitate dissolving of the CO into the liquid composition.

While not required, in embodiments relating to commercial production of the liquid composition, it is preferred that the CO-containing liquid composition be sealed in a CO-impermeable container to preclude loss of dissolved CO over time. Accordingly, in embodiments, the method of making a CO-containing liquid composition comprises dispensing the liquid composition into a sealable CO-impermeable container and sealing the container after an appropriate amount of CO has been dissolved in the liquid composition. Dispensing of the liquid can be performed before, during, or after dissolving CO into the liquid composition. Typically, sealing will be performed under CO gas and under greater than atmospheric conditions to minimize loss of dissolved CO during the process of sealing. As such, it is preferable that the container and sealing mechanism (e.g., cap, top) are resistant to the pressures used during dissolving of CO into the composition (e.g., from about 1.1 ATM to about 8 ATM or higher). As discussed above, any number of sealable containers and caps are known in the art of bottling and canning of liquids, and any of these can be used within the context of the present invention.

The method of making a CO-containing liquid composition relies on the use of greater than atmospheric pressure (i.e., "high" pressure) to increase the amount of CO dissolved in the liquid composition. According to the invention, at least 1.1 atmospheres (ATM) of pressure is used in the process of introducing CO into the liquid composition. Preferably, where high pressure is used, at least 1.2 ATM is used. In certain exemplary embodiments, 2 ATM, 3 ATM, or 5 ATM is used during introduction of CO into the liquid composition. It is contemplated by the invention that pressures above 5 ATM are also suitable, such as 6 ATM, 7 ATM, 8 ATM, and 10 ATM or higher. In accordance with the discussion concerning ranges set forth above, the skilled artisan will recognize that all specific values, and all possible ranges, falling within the atmospheric conditions discussed herein are contemplated as part of the invention, and that there is no need to specifically recite each and every possible value and range in order for the skilled artisan to recognize that all such values and ranges are envisioned as part of the invention. Furthermore, it is to be understood that variations in the source of CO, the equipment used to introduce the CO into the liquid composition, the pressure of the CO being used (i.e., volume supplied per unit time), and the atmospheric pressures used will affect the amount of time required to achieve a suitable concentration of CO in the composition. Those of skill in the art can easily identify the correct parameters to achieve a CO-containing composition using only standard, straightforward procedures known in the art, without any undue or excessive experimentation.

The method of making a CO-containing liquid composition preferably comprises subjecting the composition to a low temperature during the step of exposing the liquid to CO. It has been found that lowering the temperature from ambient room temperature (about 21° C.) to about 2° C. increases the amount of CO that is dissolved in the liquid composition. According to the invention, a low temperature is a temperature at or below 4° C., preferably at or below 2° C., such as 1° C., 0° C., −1° C., −2° C., −3° C., −4° C., −5° C., −6° C., −10° C., −12° C., −14° C., −16° C., −18°, −20° C., or below. In embodiments where the composition is exposed to a low temperature, it is preferred that the CO-containing liquid composition be sealed to preclude loss of dissolved CO over time. Accordingly, in embodiments, the method of making a CO-containing liquid composition comprises dispensing the liquid composition into a sealable container and sealing the container after an appropriate amount of CO has been dissolved in the liquid composition. Dispensing of the liquid can be performed before, during, or after dissolving CO into the liquid composition. Typically, sealing will be performed under low temperature to minimize loss of dissolved CO during the process of sealing. As discussed above, any number of sealable containers and caps are known in the art of bottling and canning of liquids, and any of these can be used within the context of the present invention. For the sake of clarity, in embodiments where both high pressure and low temperature are used, it is preferred that sealing be performed under both high pressure and low temperature, although the same pressure and temperature used for dissolving CO into the liquid need not be used. Further, it is to be understood that, once the CO-containing liquid is sealed in a container under CO gas, it is not necessary to maintain the sealed container at high pressure and low temperature, as the sealed container will not allow dissolved CO to escape from solution.

The present invention identifies three important parameters for achieving a liquid composition having a therapeutically- and/or prophylactically-effective amount of dissolved gaseous CO: introducing gaseous CO under high pressure; introducing gaseous CO under low temperature; and the presence of complex substances in the liquid composition. However, it is to be understood that other parameters can be adjusted to improve or otherwise alter the concentration of CO in solution, or simply to alter the overall taste and consistency. These parameters can be adjusted for any number of reasons, including, but not limited to: altering the taste of the liquid; altering the sweetness, tartness, or tang of the liquid; altering the pH of the liquid; altering the salinity of the liquid; and altering the consistency of the liquid. It has been found that alterations in many parameters do not significantly affect the overall CO carrying capacity of a liquid composition, with the main exceptions of alteration of pressure, temperature, and presence of complex components, as described above. For example, tests show that, for a given pressure, temperature, and complex component combination, variations in pH, simple sugar concentrations, and salt concentrations have little effect on dissolved CO levels. Accordingly, the practitioner may adjust various parameters to suit a particular need without departing from the concept of the invention.

EXAMPLES

The invention will be further explained by the following Examples, which are intended to be purely exemplary of the invention, and should not be considered as limiting the invention in any way.

Example 1

Exemplary Formulations

The present invention provides an advancement over the prior art by providing a liquid composition comprising therapeutically- and/or prophylactically-effective amounts of dissolved gaseous CO in dosage forms. The formulations are based on three main criteria: the level of gas-phase pressure during dissolving of CO into the liquid composition; the temperature during dissolving of CO into the liquid composition; and the presence of complex components in the liquid composition. Tables 3-5 show data indicating the role of proteins, fats, and other complex components in raising the dissolved CO concentration in liquid compositions according to the present invention.

Referring to Table 3, it can be seen that CO can be dissolved in liquid compositions comprising fats and proteins (Ensure® (Abbott, Abbott Park, Ill.), 10%-50% in water) and standard cream from cow milk (50% cream in water, v/v) at concentrations higher than achievable in water alone, on the order of at least 28 mg/l. Although improved dissolved CO concentrations can be achieved at 1 ATM and 21° C. using low levels of proteins and fats (e.g., 10% Ensure®), the amount of dissolved CO can be increased by increasing the amounts of proteins and fats, and by increasing the gas-phase pressure applied during the dissolving process.

TABLE 3

CO Concentrations with Various Protein and Fat Containing Solutions
(~1 atmosphere pressure; Solutions in Water)

| Solution | Temperature | CO Concentration (mg/L) | N |
|---|---|---|---|
| 10% Ensure ® | ~21° C. | 28.1 | 3 |
| 20% Ensure ® | ~21° C. | 34.2 | 5 |
| 30% Ensure ® | ~21° C. | 43.2 | 4 |
| 40% Ensure ® | ~21° C. | 46.3 | 2 |
| 50% Ensure ® | ~21° C. | 59.8 | 2 |
| 50% Cream | ~21° C. | 63.9 | 10 |
| 50% Cream | ~2° C. | 74.9 | 10 |

Looking now at Table 4, one can see that the amount of pressure provided during the process of dissolving CO into a water-containing liquid composition is an important factor in achieving a composition with therapeutic levels of CO. More specifically, Table 4 shows that, for a given percent of Ensure® or standard cream, increasing the pressure during dissolving of CO results in a significant increase in the amount of CO infused into the composition.

TABLE 4

CO Concentrations with Protein and Fat Containing Solutions at
Various Pressures
(Solutions in Water)

| Solution | Temp. | Pressure | CO Concentration (mg/L) |
|---|---|---|---|
| 50% Ensure ® | ~21° C. | 1 ATM | 60 |
| 50% Ensure ® | ~21° C. | 2 ATM | 120 |
| 50% Ensure ® | ~21° C. | 3 ATM | 180 |
| 50% Ensure ® | ~21° C. | 5 ATM | 300 |
| 50% Ensure ® | ~21° C. | 10 ATM | 600 |
| 50% Cream | ~2° C. | 1 ATM | 75 |
| 50% Cream | ~2° C. | 2 ATM | 150 |
| 50% Cream | ~2° C. | 3 ATM | 225 |
| 50% Cream | ~2° C. | 5 ATM | 375 |
| 50% Cream | ~2° C. | 10 ATM | 750 |

Table 5 shows a comparison of the amounts of liquid composition needed to provide a therapeutic dose of CO to non-SCD subjects (referred to as "normal" patients) using aqueous compositions and compositions comprising proteins and fats (i.e., a 50% cream composition). As can be seen from the Table, the volume of composition needed to be administered is one-half or less for liquid compositions comprising proteins and fats as compared to simple aqueous compositions.

TABLE 5

Volumes Necessary to Achieve a Therapeutic Dose of CO in Normal Patients
(Therapeutic dose assumed at an average increase of 5% CO-Hb)

| Temperature, Pressure | CO Concentration in Aqueous Solution (mg/L water) | Necessary Daily Volume of Aqueous Solution to Achieve Average Increase of 5% CO-Hb | CO Concentration in Non-aqueous Solution (mg/L water) | Necessary Daily Volume of Non-Aqueous Solution (50% Cream) to Achieve Average Increase of 5% CO-Hb |
|---|---|---|---|---|
| 2° C.; 1 ATM | 40 | 8.4 L | 75 | 3.6 L |
| 2° C.; 2 ATM | 80 | 4.2 L | 150 | 1.8 L |
| 2° C.; 3 ATM | 120 | 2.8 L | 225 | 1.2 L |
| 2° C.; 5 ATM | 200 | 1.7 L | 375 | 0.7 L |
| 2° C.; 10 ATM | 400 | 0.8 L | 750 | 0.4 L |

As can be seen from Tables 3-5, compositions containing therapeutically- and prophylactically-effective levels of CO can be produced according to the present invention. Further, the methods according to the invention, and the compositions prepared using the methods, are superior in capturing CO in solution through the use of higher than 1 ATM of pressure, temperatures lower than 21° C., and compositions comprising complex substances, such as proteins and/or fats.

Example 2

In vivo Efficacy of Compositions of the Invention

The ability of compositions according to the present invention to deliver therapeutic levels of CO to the bloodstream of humans and rats has been established, as reported in this Example. More specifically, an aqueous formulation was prepared by dissolving CO into water at approximately 2° C. and approximately 1.2 ATM, resulting in a composition containing a concentration of CO of 0.05 g/L. Approximately 350 ml of the CO-infused water was taken orally twice at an interval of 1.5 hours by the normal volunteer, with the following results (Table 6). These results align to the expected stoichiometric results within expected error bands and loss of CO over time:

TABLE 6

Concentration of CO-Hb in blood of normal subject after dosing

| Time (hours) | Concentration (% CO-Hb) |
|---|---|
| 0 (baseline) | 1.7 |
| 1.5 | 2.8 |
| 3.0 | 3.4 |

This experiment shows not only that therapeutically-effective levels of CO can be infused into liquid compositions according to the invention, but that such compositions can be orally ingested and can deliver therapeutic doses of CO to the bloodstream, as assayed by CO-Hb concentrations.

To further show the effectiveness of the present invention in creating therapeutically-effective liquid compositions for delivery of CO, a liquid composition comprising protein and fat was prepared according to the process of the invention, and was tested for its CO-delivering activity in rats. More specifically, a formulation of 50% cream in water was prepared and CO was introduced into it at approximately 2° C. and approximately 1.2 ATM, resulting in a composition having a concentration of 0.075 g/L (75 mg/l). Three (3) ml. of the formulation was administered to rats by way of gavage, and the resulting CO-Hb levels were assayed and compared to a negative control that received a non-CO containing liquid via gavage.

More specifically, laboratory rats weighing 250-300 grams were treated by gavage with either: 1) no gavage (negative control); 2) 3 ml of CO-infused water twice at times 0 and 1 hour; and 3) 3 ml of CO-infused 50% cream twice at times 0 and about 1.25 hours. Blood sampling was carried out at approximately 1.5 hours after the second gavage for each rat.

The results of the tests are presented in Table 7. The results show that CO can be delivered to the rat bloodstream in an amount that is effective to treat diseases and disorders associated with CO-effective outcomes via an oral route using compositions according to the present invention. Similar results to those presented in Table 7 were obtained with a composition comprising 40% Ensure® prepared and administered in the same fashion as the 50% cream.

TABLE 7

Delivery of Therapeutically Effective Amounts of CO In Vivo

| Specimen | Concentration at Assay Point (% CO-Hb) |
|---|---|
| Neg. Control | 0.8 ± 1.9% |
| 2 | 3.0 ± 1.1 |
| 3 | 4.3 ± 0.6 |

The present Example thus shows that compositions according to the present invention can be successfully used preclinically in vivo to deliver therapeutically-effective amounts of CO to the blood of subjects.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification be considered as exemplary only, with the true scope of the invention indicated by the following claims.

REFERENCES

Aroutiounian, S et al., "Evidence for carbon monoxide binding to sickle cell polymers during melting." Biophysical Chemistry 91 (2001) 167-181.

Akamatsu, Y., M. Haga, et al. (2004). "Heme oxygenase-1-derived carbon monoxide protects hearts from transplant associated ischemia reperfusion injury." Faseb J 18(6): 771-2.

Bauer, Inge et al., "Bench-to-bedside review: Carbon monoxide—from mitochondrial poisoning to therapeutic use." Critical Care 2009, 13:220

Beckman J, Belcher, JD, et al. "Inhaled carbon monoxide reduces leukocytosis in a murine model of sickle cell disease." Am J Physiol Heart Circ Physiol 297: H1243-H1253, 2009.

Beutler E. The effect of carbon monoxide on red cell life span in sickle cell disease. Blood 46: 253-259, 1975.

Bunn, H. F. (1997). "Pathogenesis and treatment of sickle cell disease." N Engl J Med 337(11): 762-9.

Clark, J. E., P. Naughton, et al. (2003). "Cardioprotective actions by a water-soluble carbon monoxide-releasing molecule." Circ Res 93(2): e2-8.

EMA COMMITTEE FOR MEDICINAL PRODUCTS FOR HUMAN USE (CHMP), "GUIDELINE ON THE SPECIFICATION LIMITS FOR RESIDUES OF METAL CATALYSTS OR METAL REAGENTS", London, 21 Feb. 2008, Doc. Ref. EMEA/CHMP/SWP/4446/2000

Foresti R et al., "Use of carbon monoxide as a therapeutic agent: promises and challenges", Intensive Care Med. 2008 Apr;34(4):649-58. Epub 2008 Feb. 20

Guo, Y., A. B. Stein, et al. (2004). "Administration of a CO-releasing molecule at the time of reperfusion reduces infarct size in vivo." Am J Physiol Heart Circ Physiol 286(5): H1649-53.

Hampson N B, Hauff N M: Carboxyhemoglobin levels in carbon monoxide poisoning: do they correlate with the clinical picture? Am J Emerg Med 2008, 26:665-669.

Ikeda, A. et. al. "Liver graft exposure to carbon monoxide during cold storage protects sinusoidal endothelial cells and emeliorates reperfusion injury in rats", Liver Transpl. 2009 November ; 15(11): 1458-1468.

Kaczorowski D J, Zuckerbraun B S. Carbon monoxide: medicinal chemistry and biological effects. Curr Med Chem 14: 2720-2725, 2007.

Kohmoto, J., A. Nakao, et al. (2007). "Carbon monoxide protects rat lung transplants from ischemia-reperfusion injury via a mechanism involving p38 MAPK pathway." Am J Transplant 7(10): 2279-90.

Motterlini, R., Otterbein L., "The therapeutic potential of carbon monoxide", Nat Rev Drug Discov. 2010 Sep;9(9): 728-43

Nakao, A., J. S. Neto, et al. (2005). "Protection against ischemia/reperfusion injury in cardiac and renal transplantation with carbon monoxide, biliverdin and both." Am J Transplant 5(2): 282-91.

Nakao A et. al. "Ex vivo application of carbon monoxide in University of Wisconsin solution to prevent intestinal cold ischemia/reperfusion injury. Am J Transplant. 2006; 6(10):2243-2255.

Nakao, A. , et. al., "A Single Intraperitoneal Dose of Carbon Monoxide-Saturated Ringer's Lactate Solution Ameliorates Postoperative Ileus in Mice", JPET 319:1265-1275, 2006

Nakao A et. al. "Ex vivo carbon monoxide prevents cytochrome P450 degradation and ischemia/reperfusion injury of kidney grafts". Kidney International. 2008; 74:989-991

Natanson C, et. al. "Cell-free hemoglobin-based blood substitutes and risk of myocardial infarction and death: a meta-analysis", JAMA. 2008 May 21;299(19):2304-12

Neto, J. S., Nakao, A. et al. (2004). "Protection of transplant-induced renal ischemia-reperfusion injury with carbon monoxide." Am J Physiol Renal Physiol 287(5): F979-89.

Piantadosi C A: Biological chemistry of carbon monoxide. Antioxid Redox Signal 2002, 4:259-270.

Platt O S, Brambilla D J, Rosse W F, et al. Mortality in sickle cell disease. Life expectancy and risk factors for early death. N Engl J Med. 1994;330(23):1639-1644.

Platt O S, Thorington B D, Brambilla D J, et al. Pain in sickle cell disease. Rates and risk factors. N Engl J Med. 1991;325(1):11-16.

Rodkey F L, O'Neal J D, Collison H A, Uddin D E: Relative affinity of hemoglobin S and hemoglobin A for carbon monoxide and oxygen. Clin Chem 1974, 20:83-84.

Sirs, J. A. (1963). "The use of carbon monoxide to prevent sickle-cell formation." Lancet 1(7288): 971-2.

Stein, A. B., Y. Guo, et al. (2005). "Administration of a CO-releasing molecule induces late preconditioning against myocardial infarction." J Mol Cell Cardiol 38(1): 127-34.

Stewart R D. The effect of carbon monoxide on humans. Annu Rev Pharmacol 15: 409-423, 1975.

Stewart R D, Peterson J E, Baretta E D, Bachand R T, Hosko M J, Herrmann A A: Experimental human exposure to carbon monoxide. Arch Environ Health 1970, 21:154-164.

Stuart, M. J. and R. L. Nagel (2004). "Sickle-cell disease." Lancet 364(9442): 1343-60.

Stupfel M, Bouley G: Physiological and biochemical effects on rats and mice exposed to small concentrations of carbon monoxide for long periods. Ann N Y Acad Sci 1970, 174:342-368.

United States Patent Application 20100311657 Abuchowski; Abraham et al. "HEMOGLOBIN COMPOSITIONS" Dec. 9, 2010

United States Patent Application 20090082257 Winslow; Robert M. "Ma1PEG-Hb conjugate-containing compositions for delivering carbon monoxide (CO) to cells" Mar. 26, 2009

Van Meter K W: Carbon monoxide poisoning. In Emergency Medicine. Edited by Tintinalli J E, Kelen G D, Stapczynski J S. New York: McGraw Hill: New York; 2003:1238-1242.

Vandegriff, K. D., M. A. Young, et al. (2008). "CO-MP4, a polyethylene glycol-conjugated haemoglobin derivative and carbon monoxide carrier that reduces myocardial infarct size in rats." Br J Pharmacol 154(8): 1649-61.

Weaver L K. Clinical Practice. Carbon monoxide poisoning. N Engl J Med 360: 1217-1225, 2009

Wu L, Wang R. Carbon monoxide: endogenous production, physiological functions, and pharmacological applications. Pharmacol Rev 57: 585-630,2005.

Yallop, D., E. R. Duncan, et al. (2007). "The associations between air quality and the number of hospital admissions for acute pain and sickle-cell disease in an urban environment." Br J Haemato1 136(6): 844-8.

Zuckerbraun, B. S., C. A. McCloskey, et al. (2005). "Carbon monoxide prevents multiple organ injury in a model of hemorrhagic shock and resuscitation." Shock 23(6): 527-32.

The invention claimed is:

1. A liquid composition comprising dissolved gaseous carbon monoxide (CO) and CO gaseous bubbles in an amount of 85 mg/l or more in a liquid, for use as a therapeutic or prophylactic agent in the treatment of diseases and disorders treatable with CO, wherein the CO gas bubbles are in contact with the liquid when the liquid is at ambient pressure, and wherein the liquid composition is a liquid colloidal dispersion, liquid suspension, emulsion, or foam, and the composition further comprises at least one of: protein, complex carbohydrate, sugar, artificial sugar substitute, fruit juice, carbohydrate, cellulose, fiber, citric acid, artificial flavoring, natural flavoring, gum, pectin, ascorbic acid, preservative, saponin, and a salt.

2. A method of treating a subject suffering from or at risk of developing a disease that is treatable with CO, said method comprising:

administering to the subject a liquid composition of claim 1 in an amount of at least 85 mg/l, which is an amount sufficient to reduce or eliminate at least one clinical symptom of the disease, prevent development or recurrence of the disease, limit morbidities from the disease, or cure the disease, wherein administering is by way of the gastrointestinal (GI) tract.

3. The method of claim 2, wherein the liquid composition comprises dissolved gaseous CO in an amount of from 100 mg/l to 400 mg/l.

4. The method of claim 2, wherein the liquid composition comprises dissolved gaseous CO in an amount of from 125 mg/l to 4000 mg/l.

5. The method of claim 2, wherein the volume of the liquid composition administered per day is 2 liters or less.

6. The method of claim 2, wherein the volume of the liquid composition administered per day is 1 liter or less.

7. The method of claim 2, wherein administration is by oral ingestion.

8. The method of claim 2, wherein the disease is: an inflammatory disease, an ischemic disease, sepsis, a cardiovascular disease, kidney disease, liver disease, or a gastrointestinal disease.

9. The method of claim 2, wherein the disease is a hematologic disease.

10. The method of claim 9, wherein the hematological disease is caused by an abnormal hemoglobin.

11. The method of claim 10, wherein the disease is Sickle Cell Disease, Hemoglobin C Disease, Hemoglobin SC Disease, or Hemoglobin S beta-thalassemia.

12. The method of claim 2, wherein administering is repeated one or more times to provide a treatment regimen.

* * * * *